United States Patent [19]

Richardson

[11] 4,206,234

[45] Jun. 3, 1980

[54] TRIPHENYLBUT-1-ENE DERIVATIVES AND PHARMACEUTICAL COMPOSITIONS AND USES THEREOF

[75] Inventor: Dora N. Richardson, Macclesfield, England

[73] Assignee: Imperial Chemical Industries Limited, London, England

[21] Appl. No.: 926,319

[22] Filed: Jul. 20, 1978

[30] Foreign Application Priority Data

Aug. 22, 1977 [GB] United Kingdom ............... 35094/77

[51] Int. Cl.$^2$ .................... A61K 31/135; C07C 87/28; C07C 91/16; C07C 93/08
[52] U.S. Cl. ................................. 424/330; 260/570 R
[58] Field of Search .................... 424/330; 260/570 R

[56] References Cited

U.S. PATENT DOCUMENTS

| | | | |
|---|---|---|---|
| 2,914,561 | 11/1959 | Allen et al. | 424/330 |
| 3,168,565 | 2/1965 | Palopoli et al. | 424/570 R |
| 3,288,806 | 11/1966 | DeWald | 260/570 R |
| 3,493,606 | 2/1970 | Richardson | 260/570 R |
| 4,061,733 | 12/1977 | Gunjikar | 424/330 |

OTHER PUBLICATIONS

Xenobiotica (1973), 3, p. 693.
Nature 212, p. 87 (1966)—Harper et al.
Nature 212, 733–734 (1966)—Bedford et al.

*Primary Examiner*—Douglas W. Robinson
*Attorney, Agent, or Firm*—Cushman, Darby & Cushman

[57] ABSTRACT

The disclosure relates to the compound 1-(p-β-dimethylaminoethoxyphenyl)-cis-1-(p-hydroxyphenyl)-2-phenylbut-1-ene, to pharmaceutical compositions containing it and to the use of the compound to produce an anti-oestrogenic effect in warm-blooded animals.

8 Claims, No Drawings

TRIPHENYLBUT-1-ENE DERIVATIVES AND PHARMACEUTICAL COMPOSITIONS AND USES THEREOF

This invention relates to a triphenylbut-1-ene derivative and the use of the compound or compositions containing it as an anti-oestrogen.

It is known from J. Reprod. Fert. (1967), 13, 101 that 1-(p-β-dimethylaminoethoxyphenyl)trans-1,2-diphenylbut-1-ene (tamoxifen) shows anti-oestrogenic activity in rats and, in this species, is weakly and atypically oestrogenic. It is also known from Xenobiotica (1973), 3, 693, that 1-(p-β-dimethylaminoethoxyphenyl)trans-1-(p-hydroxyphenyl)-2-phenylbut-1-ene is a major metabolite of tamoxifen in the dog, but the pharmacological properties of this compound have not been described.

We have now found that 1-(p-β-dimethylaminoethoxyphenyl)-cis-1-(p-hydroxyphenyl)-2-phenylbut-1-ene (compound I) shows anti-oestrogenic activity of the same order as that shown by tamoxifen, but in contrast to the oestrogenic activity expected in a hydroxy compound of this type, and especially in a cis isomer by analogy with the cis isomer of tamoxifen, compound I shows only the weak and atypical oestrogenic activity also shown by tamoxifen.

In this specification, the designations "cis" and "trans" refer to the relative positions of the p-hydroxyphenyl group and the unsubstituted phenyl group about the double bond.

According to the invention there is provided a method of producing an anti-oestrogenic effect in warm blooded animals, including man, which require such treatment, which comprises administering orally or parenterally to such a warm blooded animal, an effective amount of compound I or a pharmaceutically acceptable salt thereof.

The anti-oestrogenic activity of compound I has been demonstrated by its effect in preventing implantation of the fertilised ovum when administered by intraperitoneal injection to rats at a dose of 0.02 mg./kg. on each of days 3, 4 and 5 of pregnancy, or when dosed orally at 0.15 mg./kg. on day 4. Anti-oestrogenic activity has also been demonstrated by its effect in inhibiting oestradiol-induced vaginal cornification in ovariectomised rats.

The weak oestrogenic activity of compound I has been demonstrated by its effect in producing cornified vaginal smears in sprayed rats at doses of 20–40 mg./kg. on each of three days.

A compound with the above pharmacological properties is of value in the treatment of the same conditions in which tamoxifen is beneficial, in particular, in the treatment of anovulatory infertility and in the treatment of breast tumours.

When used to produce an anti-oestrogenic effect in warm blooded animals, a typical daily dose is from 0.05 to 1 mg./kg. administered orally, or by injection. In man this is equivalent to an oral dose of from 5–80 mg./day. In use, tamoxifen has been administered orally at doses of from 20–80 mg./day for the treatment of anovulatory infertility, and at doses from 10–40 mg./day for the treatment of breast tumours. A similar regime is appropriate for the administration of compound I, most conveniently in the form of a pharmaceutical composition.

According to a further feature of the invention, there is provided a pharmaceutical composition comprising compound I or a pharmaceutically acceptable salt thereof together with a pharmaceutically acceptable diluent or carrier.

A particularly suitable salt is, for example a hydrochloride, sulphate, phosphate, acetate, tartrate or citrate.

The composition may be in a form suitable for oral or parenteral administration. A tablet or capsule is a particularly convenient form for oral administration, and such a composition may be made by conventional methods and contain conventional excipients. Thus a tablet could contain diluents, for example mannitol or maize starch, disintegrating agents, for example alginic acid, binding agents, for example methylcellulose, and lubricating agents, for example magnesium stearate.

A composition for oral administration may conveniently contain from 5–50 mg. of compound I, preferably 5–20 mg.

Compound I is believed to be a novel compound and it is provided as a further feature of the invention.

Compound I may be obtained by the processes which are applicable to the manufacture of analogous compounds. Thus, for example, the alkanol 1-(p-β-dimethylaminoethoxyphenyl)-1-(p-hydroxyphenyl)-2-phenylbutan-1-ol or 1-(p-β-dimethylaminoethoxyphenyl)-1-[p-(2-tetrahydropyranyloxy)phenyl]-2-phenylbutan-1-ol may be dehydrated with an acid, for example hydrochloric acid, conveniently in a solvent, for example ethanol, at a temperature of from 20° C. to 80° C. to give the corresponding alkene, usually as a mixture of the cis and trans isomers. Compound I is then isolated by fractional crystallisation of the mixture or by chromatography.

The alkanols used as starting material, may be obtained in several ways, for example, (a) p-(2-tetrahydropyranyloxy)phenyl magnesium bromide may be reacted with 4-(β-dimethylaminoethoxy)-α-ethyldesoxybenzoin, (b) p-β-dimethylaminoethoxyphenyl bromide may be reacted with 4-(2-tetrahydropyranyloxy)-α-ethyldesoxybenzoin in the presence of n-butyl lithium, or with 4-benzyloxy-α-ethyldesoxybenzoin followed by removal of the benzyl group by hydrogenolysis, or (c) an excess of p-β-dimethylaminoethoxyphenyl magnesium bromide may be reacted with 4-hydroxy-α-ethyldesoxybenzoin.

The invention is illustrated but not limited by the following Examples

EXAMPLE 1

Tablets were made by granulating a mixture of 1-(p-β-dimethylaminoethoxyphenyl)-cis-1-(p-hydroxyphenyl)-2-phenylbut-1-ene (compound I) or its citrate with mannitol and maize starch in the presence of alginic acid and then mixing the dried granules with methylcellulose and magnesium stearate followed by compression into tablets. A typical tablet had the composition:

Compound I: 10 mg.
Mannitol: 111 mg.
Maize starch: 15 mg.
Alginic acid: 6 mg.
Methyl cellulose: 0.75 mg.
Magnesium stearate: 1.5 mg.

EXAMPLE 2

A solution of 1-(p-β-dimethylaminoethoxyphenyl)-1-[p-(2-tetrahydropyranyloxy)phenyl]-2-phenylbutan-1- ol (11 g.) in ethanol (100 ml.) was acidified with concentrated hydrochloric acid and heated under reflux for 2 hours. The solvent was evaporated and the residue was stirred with water and made alkaline with ammonia solution. The precipitated material was extracted with ether, and the ethereal extract was dried and evaporated to give a mixture of the isomers of 1-(p-β-dimethylaminoethoxyphenyl)-1-(p-hydroxyphenyl)-2-phenylbut-1-ene. This mixture (ca. 10 g.) was stirred with chloroform (100 ml.) and the mixture filtered. The filtrate was evaporated and the residue again stirred with chloroform and filtered. The filtrate was evaporated and the residue crystallized from acetone to give 1-(p-β-dimethylaminoethoxyphenyl)-cis-1-(p-hydroxyphenyl)-2-phenylbut-1-ene (100 mg.), m.p. 172°–174° C.

The butan-1-ol derivative used as starting material was prepared as follows:

(a) A solution of p-(2-tetrahydropyranyloxy)phenyl magnesium bromide was prepared in the usual manner from magnesium (1.65 g.) and p-(2-tetrahydropyranyloxy)phenyl bromide (8.48 g.) in a mixture of dry ether (30 ml.) and dry tetrahydrofuran (30 ml.). To this solution was added a solution of 4-(β-dimethylaminoethoxy)-α-ethyldesoxybenzoin (9.33 g.) in ether (50 ml.). The mixture was heated under reflux for 2 hours, cooled and decomposed by the addition of saturated ammonium chloride solution. The organic layer was separated, and the aqueous layer was extracted with ether. The extract was combined with the organic layer, dried and evaporated to give 1-(p-β-dimethylaminoethoxyphenyl)-1-[p-(2-tetrahydropyranyloxy)phenyl]-2-phenylbutan-1-ol as an oil used without further purification.

(b) A 1.25 M. solution of n-butyl-lithium in hexane (26 m.) was added under nitrogen to a solution of p-β-dimethylaminoethoxyphenyl bromide (6.1 g.) in ether (60 ml.). The mixture was cooled to −20° C. and a solution of 4-(2-tetrahydropyranyloxy)-α-ethyldesoxybenzoin (8.1 g., m.p. 82°–84° C. obtained from 2,3-dihydropyran and 4-hydroxy-α-ethyldesoxybenzoin in the presence of toluene-p-sulphonic acid) in ether (120 ml.) was added dropwise. The mixture was allowed to reach room temperature, and water (100 ml.) added. The organic layer was separated and extracted with 5% aqueous acetic acid (3×100 ml.). The extract was treated with charcoal, filtered and the filtrate made alkaline with ammonia solution. The precipitated base was extracted with chloroform and the extract dried and evaporated. The residue was crystallised from petrol (b.p. 100°–120° C.) to give 1-(p-β-dimethylaminoethoxyphenyl)-1-[p-(2-tetrahydropyranyloxy)phenyl]-2-phenylbutan-1-ol (5.5 g.), m.p. 128°–132° C.

EXAMPLE 3

The process of Example 2 was repeated using 1-(p-β-dimethylaminoethoxyphenyl)-1-(p-hydroxyphenyl)-2-phenylbutan-1-ol as starting material to give 1-(p-β-dimethylaminoethoxyphenyl)-cis-1-(p-hydroxyphenyl)-2-phenylbut-1-ene with the same properties as described in Example 2.

The butan-1-ol used as starting material was prepared as follows:

(a) A solution of p-β-dimethylaminoethoxyphenyl magnesium bromide was prepared in the usual way from magnesium (1.44 g.) and p-β-dimethylaminoethoxyphenyl bromide (14.64 g.) in dry tetrahydrofuran (50 ml.). To this solution was added a solution of 4-hydroxy-α-ethyldesoxybenzoin (4.8 g.) in dry tetrahydrofuran (25 ml.). The mixture was heated under reflux for 3 hours, cooled and a solution of ammonium chloride (80 g.) in water (120 ml.) added. The organic layer was separated and the aqueous layer was extracted with ether. The extract was combined with the organic layer, dried and evaporated. The residue (1.8 g.) was crystallised from benzene to give 1-(p-β-dimethylaminoethoxyphenyl)-1-(p-hydroxyphenyl)-2-phenylbutan-1-ol, m.p. 180°–182° C.

(b) A mixture of 4-hydroxy-α-ethyldesoxybenzoin (44.5 g.), sodium carbonate (18.5 g.), potassium iodide (1.4 g.) and benzyl chloride (19 ml.) in ethanol (350 ml.) and water (50 ml.) was stirred and heated under reflux for 8 hours. The mixture was cooled, filtered and the residue washed with water to give 4-benzyloxy-α-ethyldesoxybenzoin (54.3 g.), m.p. 71° C.

A 1.25M solution of n-butyl-lithium in hexane (52 ml.) was added under nitrogen to a solution of p-β-dimethylaminoethoxyphenyl bromide (12.2 g.) in dry ether (160 ml.). The mixture was cooled to −30° C. and a solution of 4-benxyloxy-α-ethyldesoxybenzoin (16.5 g.) in ether (160 ml.) was added. The mixture was allowed to reach room temperature and water (100 ml.) added. The ether layer was separated and the aqueous layer extracted with ether. The extract was combined with the ether layer and extracted with 5% aqueous acetic acid (3×100 ml.). The extract was made alkaline with aqueous sodium hydroxide solution and the precipitated solid was extracted with chloroform. The extract was dried and evaporated and the residue crystallised from petrol (b.p. 100°–120° C.) to give 1-(p-β-dimethylaminoethoxyphenyl)-1-(p-benzyloxyphenyl)-2-phenylbutan-1-ol (8.42 g.), m.p. 145°–146° C.

A solution of this butan-1-ol derivative (1.0 g.) in ethanol (250 ml.) was shaken with hydrogen in the presence of 10% palladium on carbon catalyst. When no more hydrogen was absorbed, the mixture was filtered and the filtrate evaporated. The residue was crystallised from petrol (b.p. 100°–120° C.) to give 1-(p-β-dimethylaminoethoxyphenyl)-1-(p-hydroxyphenyl)-2-phenylbutan-1-ol (650 mg.), m.p. 180° C. What we claim is:

1. A method of producing an anti-oestrogenic effect in warm blooded animals, including man, which require such treatment, which comprises administering orally or parenterally to such a warm blooded animal, an anti-oestrogenic amount of the compound 1-(p-β-dimethylaminoethoxyphenyl)-cis-1-(p-hydroxyphenyl)-2-phenylbut-1-ene or a pharmaceutically acceptable salt thereof.

2. A method as claimed in claim 1 wherein there is administered a daily dose of from 0.05 to 1 mg. per kg.

3. A pharmaceutical anti-oestrogenic composition comprising an anti-oestrogenic effective amount of 1-(p-α-dimethylaminoethoxyphenyl)-cis-1-(p-hydroxyphenyl)-2-phenylbut-1-ene or a pharmaceutically acceptable salt thereof together with a pharmaceutically acceptable diluent or carrier.

4. A composition as claimed in claim 3 wherein the salt is hydrochloride, sulphate, phosphate, acetate, tartrate or citrate.

5. A composition as claimed in claim 3 which is in the form of a tablet or capsule.

6. A composition as claimed in claim 3 which contains from 5 to 50 mg. of said compound of said salt thereof.

7. A composition as claimed in claim 6 which contains from 5 to 20 mg. of said compound or said salt thereof.

8. The compound 1-(p-β-dimethylaminoethoxyphenyl)-cis-1-(p-hydroxyphenyl)-2-phenylbut-1-ene or a pharmaceutically-acceptable salt thereof.

* * * * *